Figure 1:
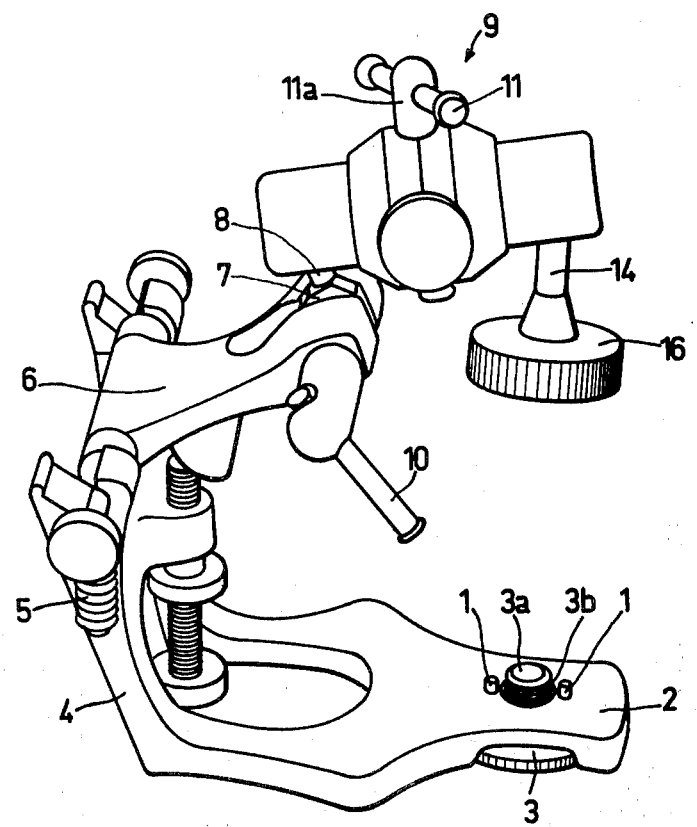

United States Patent [19]

Benzaria

[11] 4,196,518
[45] Apr. 8, 1980

[54] ARTICULATED HOLDER FOR DENTAL BRIDGE MOLDS

[76] Inventor: Clement Benzaria, Z. I. Route d'Envermeu, 76370 Neuville les Dieppe, France

[21] Appl. No.: 894,521

[22] Filed: Apr. 7, 1978

[30] Foreign Application Priority Data

Apr. 12, 1977 [FR] France .................. 77 10977

[51] Int. Cl.² .......................................... A61C 11/00
[52] U.S. Cl. .................................... 433/60; 433/64
[58] Field of Search ................................... 32/32

[56] References Cited

U.S. PATENT DOCUMENTS

| | | | |
|---|---|---|---|
| 1,670,311 | 5/1928 | Musante | 32/32 |
| 2,644,233 | 7/1953 | Shmuckler et al. | 32/32 |
| 2,765,533 | 10/1956 | McMorris | 32/32 |
| 3,844,040 | 10/1974 | Willis | 32/32 |

FOREIGN PATENT DOCUMENTS 283234  5/1950  Switzerland ........................... 32/32

*Primary Examiner*—Robert Peshock
*Attorney, Agent, or Firm*—Brisebois & Kruger

[57] ABSTRACT

This holder is characterized by a device with a double ball-and-socket joint mounted on the forward part of its holder and comprising a dual locking lever for simultaneously locking its two ball joints or selectively locking its rear ball joint, and by the use of retaining rings imbedded in the rear part of the dental bridge castings which insure their fastening on the base of the holder and on a connecting stud joined to the rear swivel joint of this holder. Used to study the articulation between dentures connected to the castings.

3 Claims, 4 Drawing Figures

ARTICULATED HOLDER FOR DENTAL BRIDGE MOLDS

The present invention has as an object an improved articulated assembly comprising especially, on its upper articulated portion, a device with a double swivel joint and with two control elements, which permit immobilizing at will, either its two ball joints, or only its rear ball joint, depending on the control element that is activated, the control elements having their respective axes of rotation oriented perpendicularly to each other, and perpendicular to the axis of two locking jaws of the ball joints.

The invention also relates to devices for attaching the dental bridge moldings or castings onto the two lower and upper extremities of the holder, such devices being in the shape of rings capable of being imbedded in appropriate positions into the plaster of these castings, and which comprise two threads, internal and external, enabling them to be fastened to the two extremities of the articulated holder.

These rings permit a better and much more rapid positioning of the casting between the two parts of the holder, than by using known methods, in which plaster was used to join these castings with the two parts of the articulated holder.

It is easily understandable in fact, that the use of a more or less large quantity of plaster in order to achieve this joining, represents an additional step detrimental to the rapid use of such a holder.

The above-mentioned rings are provided with retaining teeth set inside the plaster, and with holes for the positioning lugs or pins so that the median planes of symmetry of the casting coincide with that of the holder, and pass though the axis of the locking jaws of the double ball joint device.

The use of retaining teeth prevents any possibility of the rotation of the rings in relation to the castings in which they are imbedded, and their combination with the lug holes, and the lugs provided on the holder itself, enable, especially in the case of the lower dental bridge casting, making the plane of symmetry of this casting coincide with that of the articulated holder.

Figure 2:
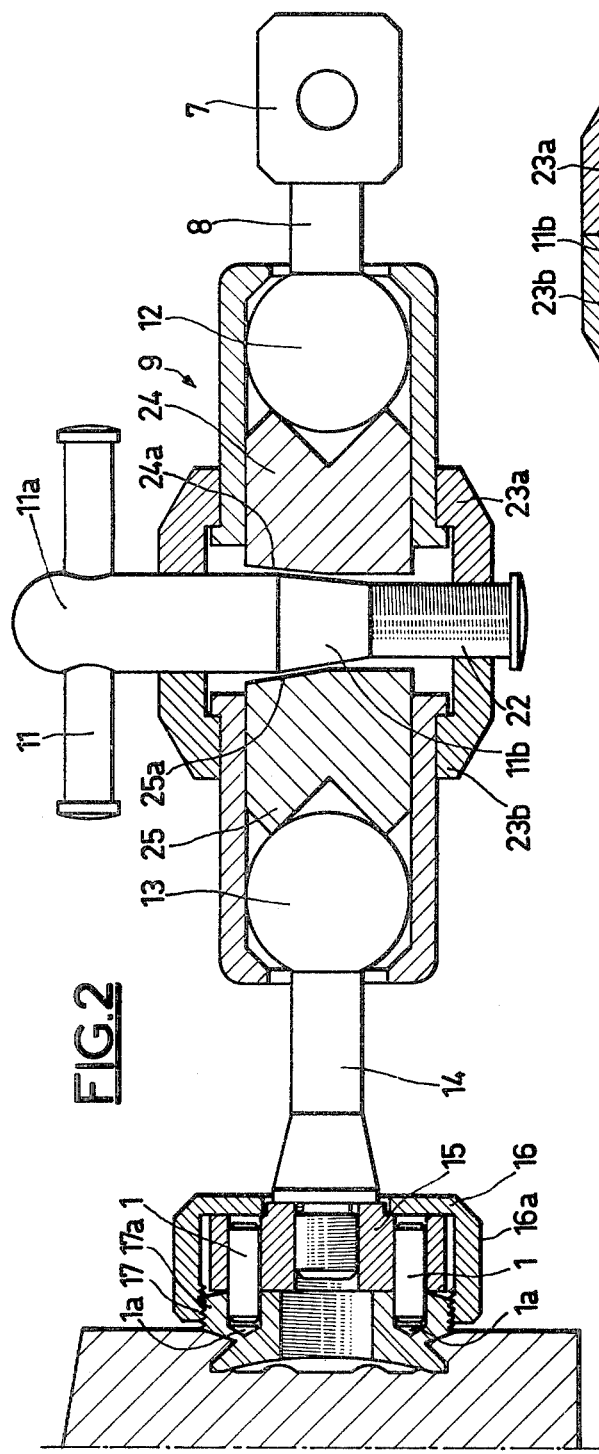
Figure 3:
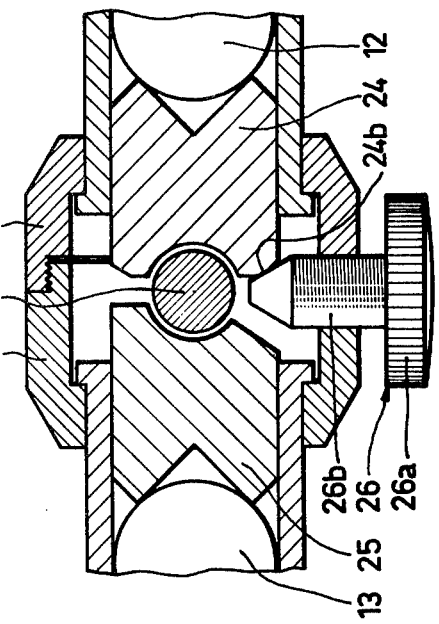
Figure 4:
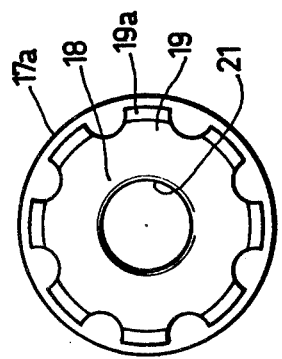

The characteristics of the present invention will be better understood by reading the description which follows of one embodiment of the holder conforming to the invention, and capable of cooperating at its two extremities with two rings of the type already mentioned, the embodiment being described by referring to the attached drawings in which:

FIG. 1 is a view in perspective of an articulated holder according to the invention, showing the devices for connecting respectively, and in suitable positions, two retaining rings imbedded in the castings, one with the lower part of one rod fixed to the forward ball joint of the two ball joint device, and the other with the forward part of base of the holder;

FIG. 2 is a view in diametrical section of the double ball joint device, showing, both the relative position of the shaft of the simultaneous locking control of the two ball joints, in relation to the rear parts of the two jaws for making these two ball joints immovable, and the mode of cooperation between the lower part of the above-mentioned rod integral with the forward ball joint and a ring imbedded in an upper dental bridge casting;

FIG. 3 is a partial view in section of the central part of the double ball joint device shown in FIG. 2, taken through the stud of the second control element which serves to lock only the rear ball joint of the double swivel joint device; and, FIG. 4 is a bottom plan view, of one of the retaining rings, from the side to be imbedded in the plaster of the castings.

The lower part of the articulated holder visible in FIG. 1, is similar to that of conventional holders, apart from two lugs 1 fixed to base 2 of the holder and situated in the vertical plane of symmetry of this base, and a knob 3, preferably knurled at its periphery, and constituting the head of a screw 3a capable of being screwed inside the internally threaded central part of a ring of the type shown in FIG. 4, imbedded in a lower dental bridge molding or casting in such a way that the corresponding lug holes of the ring have both of their axes in the plane of symmetry of the casting.

The middle part 4 of the articulated holder, which comprises especially devices with springs 5 allowing the two above dental bridge castings to be displaced slightly in relation to each other, in order to study the articulation between the dentures of the castings during chewing, is similar to the corresponding part of standard type holders.

Also similar to standard holders is the pivoting element 6, at the center of which enters the lower part 7 of a rod 8 integral with the rear swivel joint of the double swivel joint assembly 9, as is the locking lever 10 which when tightened locks the lower part 7 in relation to said element 6.

The uniqueness of the double ball and socket joint assembly 9, is that it comprises a control lever 11 capable of assuring the simultaneous locking and immobilization of the two ball joints 12 and 13 visible in particular in FIG. 2 and respectively integral with the lower part 7 of rod 8, and with a rod 14 terminated at its lower part by a cylindrical element 15 fixed to the two above-mentioned lugs 1, and onto the rear part of which a sleeve 16 can seat, and which is preferably knurled at its pheripheral part 16a and contains an internal thread 17 cooperating with the external thread 17a of a ring 18 whose forward portion comprises teeth 19, preferably equidistant, to secure the ring 18 in the plaster 20 of an upper dental bridge casting.

This ring 18 also comprises an internal thread 21 enabling it to cooperate with the external thread 3b of rod 3.

It likewise comprises lug holes 1a whose axes are placed in the plane of symmetry of a lower dental bridge casting, at the time of placement of the ring, in such a way that the plane of symmetry of this casting coincides after mounting, with that passing through the axes of the two lugs 1 visible in FIG. 1.

Concerning the device with the double swivel joints itself, it is evident that the rotation of lever 11 and of the shaft 11a which it controls, and which comprises at its forward extremity an external thread 22 cooperating with an internal thread on the sleeve in two parts 23a, 23b of device 9, acts simultaneously, by its conical part 11b, on jaws 24 and 25, through the intermediary of rear bevels 24a and 25a of jaws 24 and 25, in such a way that this rotation simultaneously immobilizes the two forward and rear swivel joints, 12 and 13.

Referring now to FIG. 3, one sees the two jaws 24 and 25 and the threaded part 22 of shaft 11a, as well as the two parts 23a and 23b of the central sleeve of the double swivel joint device 9.

Rod 26, whose head is preferably knurled at 26a, comprises a thread 26b cooperating with an internal thread provided on the two parts 23a and 23b of the above-mentioned central sleeve.

The rotation of rod 26 only acts on a bevel 24b of jaw 24, in such a way that the rear ball joint 12 becomes immobilized, while ball joint 13 continues to be able to swivel freely in all directions inside the opening of the double swivel joint device 9, between the forward part of this sleeve and the jaw 25.

One can see finally, in FIG. 4, the retaining teeth 19, whose external part is preferably chamfered at 19a, in such a way as to prevent the rotation of ring 18 inside the plaster 20. The internal threading 21 of the rings 18 is likewise visible in FIG. 4.

It is of course understood, that various changes, improvements or additions can still be made to the embodiment which has just been described, and that one can replace certain elements with equivalent elements, without altering the economic value of the invention.

I claim:

1. Articulated holder for dental bridge castings comprising:
    a first lower part and a second upper part, said two parts being hinged together, at one of their ends, by a horizontal pivot axis perpendicular to a vertical plane of symmetry of said two parts;
    first means at the other end of the lower part for rigidly securing a lower dental bridge casting to said lower part;
    second means at the other end of the upper part for securing an upper dental bridge casting to said upper part and for allowing positioning and locking said upper dental bridge casting in any position with respect to said upper part; said first and second means including respectively a threaded portion and two lugs symmetrically disposed with respect to said threaded portion, said threaded portion cooperating with a mating threaded portion and said lugs cooperating with two lug holes symmetrically disposed with respect to said mating threaded portion on a retaining ring at least partially imbedded in the corresponding dental bridge casting so that said two lug holes are located in the plane of symmetry of said dental bridge casting,
    said threaded portion and said lugs of said lower part being located in a fixed position on said lower part, in the vertical plane of symmetry of said part;
    said threaded portion and said lugs of the said upper part being located in a fixed position on a first ball element of a double ball joint device whose second ball element is hinged to said upper part about a pivot axis parallel to said pivot axis of said two parts and is able to be locked on said upper part, said double ball joint device comprising a first control element for simultaneously locking said two ball elements and a second control element for locking only said second ball element.

2. An articulated holder according to claim 1, wherein said double ball joint device comprises:
    two locking jaws slidable in a middle sleeve containing at its two opposite ends the balls of said two ball elements, said jaws having symmetrical bevels at their facing ends, and the jaw cooperating with said second ball element having a further bevel at its end facing the corresponding end of the other jaw;
    a first rod extending through said sleeve, perpendicularly to the axis of said sleeve and symmetrically between the said facing ends of said jaws, and having an external control head, a threaded portion cooperating with a threaded hole of said sleeve and a truncated portion acting on said bevels of said two jaws upon screwing said rod to simultaneously lock both said jaws, and
    a second rod perpendicular to said first rod and perpendicular to the axis of said sleeve, having an external control head, a threaded portion cooperating with a threaded hole of said sleeve and a truncated end portion acting, upon screwing of said second rod, on said further bevel of said locking jaw of said second ball element while remaining always spaced from said locking jaw of said first ball element, so that only said second ball element is locked by screwing said second rod.

3. Articulated holder according to claim 1, wherein said retaining rings further comprise, on their portion to be imbedded in the dental bridge castings, peripheral teeth whose external portions are chamfered.

* * * * *